(12) United States Patent
Thyagarajan et al.

(10) Patent No.: US 11,110,289 B2
(45) Date of Patent: Sep. 7, 2021

(54) MICRO COILS SUITABLE FOR MAGNETIC NEURAL STIMULATION

(71) Applicant: Palo Alto Research Center Incorporated, Palo Alto, CA (US)

(72) Inventors: Krishnan Thyagarajan, Mountain View, CA (US); George Daniel, Palo Alto, CA (US); Bernard D. Casse, Saratoga, CA (US)

(73) Assignee: Palo Alto Research Center Incorporated, Palo Alto, CA (US)

(*) Notice: Subject to any disclaimer, the term of this patent is extended or adjusted under 35 U.S.C. 154(b) by 581 days.

(21) Appl. No.: 15/922,693

(22) Filed: Mar. 15, 2018

(65) Prior Publication Data

US 2019/0282825 A1 Sep. 19, 2019

(51) Int. Cl.
| | |
|---|---|
| *A61N 2/02* | (2006.01) |
| *A61N 2/00* | (2006.01) |
| *A61B 5/24* | (2021.01) |
| *A61N 1/372* | (2006.01) |
| *A61N 1/40* | (2006.01) |

(52) U.S. Cl.
CPC .............. *A61N 2/02* (2013.01); *A61B 5/24* (2021.01); *A61N 2/006* (2013.01); *A61N 1/37211* (2013.01); *A61N 1/40* (2013.01)

(58) Field of Classification Search
CPC ....... A61B 5/04001; A61N 2/006; A61N 2/02
See application file for complete search history.

(56) References Cited

U.S. PATENT DOCUMENTS

| | | | |
|---|---|---|---|
| 7,103,413 | B2 | 9/2006 | Swanson et al. |
| 8,412,332 | B2 | 4/2013 | Massoud-Ansari et al. |
| 8,761,898 | B2 | 6/2014 | Jaroch et al. |
| 8,972,004 | B2 | 3/2015 | Simon et al. |
| 9,179,875 | B2 | 11/2015 | Hua |
| 9,669,208 | B2 | 6/2017 | Harberts et al. |
| 2004/0181261 | A1 | 9/2004 | Manne |
| 2009/0157147 | A1 | 6/2009 | Cauller et al. |
| 2010/0274313 | A1 | 10/2010 | Boling et al. |
| 2011/0152967 | A1 | 6/2011 | Simon et al. |
| 2011/0288615 | A1 | 11/2011 | Armstrong et al. |
| 2014/0031914 | A1* | 1/2014 | Mashiach ............ A61N 1/3611 607/134 |
| 2015/0080637 | A1 | 3/2015 | Bonmassar et al. |
| 2015/0328477 | A1 | 11/2015 | Gale et al. |
| 2016/0129276 | A1 | 5/2016 | Fried et al. |
| 2017/0202467 | A1 | 7/2017 | Zitnik et al. |
| 2017/0312535 | A1 | 11/2017 | Kim et al. |

OTHER PUBLICATIONS

EP Patent Application No. 19162392.5; European Search Report dated Jul. 25, 2019; 7 pages.

(Continued)

*Primary Examiner* — Christine H Matthews
(74) *Attorney, Agent, or Firm* — Mueting Raasch Group

(57) ABSTRACT

An implantable magnetic neurostimulation probe includes at least one electrical conductor disposed on a substrate and arranged in at least one planar loop. At least one planar magnetic core comprising a magnetic material is disposed on the substrate and within the planar loop. A biocompatible coating is disposed over the substrate, electrically conductive trace, and magnetic core.

23 Claims, 14 Drawing Sheets

(56) References Cited

OTHER PUBLICATIONS

Bonmassar et al., "EM fields Comparison between Planar vs. Solenoidal μMS Coils Designs for Nerve Stimulation", IEEE, 2017, pp. 3576-3579.
Bonmassar et al., "Optimizing Microscopic Magnetic Fields for Neural Stimulation", International Journal of Bioelectromagnetism, Vo. 16, No. 1, 2014, pp. 1-31.
Bonmassar et al., "Microscopic magnetic stimulation of neural tissue", Nature Communications, Jun. 26, 2012, 10 pages.
Freeman et al., "A Sub-millimeter, Inductively Powered Neural Stimulator", Frontiers in Neuroscience, Nov. 27, 2017, pp. 1-12.
Lee et al., "Implantable microcoils for intracortical magnetic stimulation", Science Advances, Dec. 9, 2016, 20 pages.
RamRakhyani et al., "Ferrite core non-linearity in coils for magnetic neurostimulation", Healthcare Technology Letters, vol. 1, No. 4, 2014, pp. 87-91.

* cited by examiner

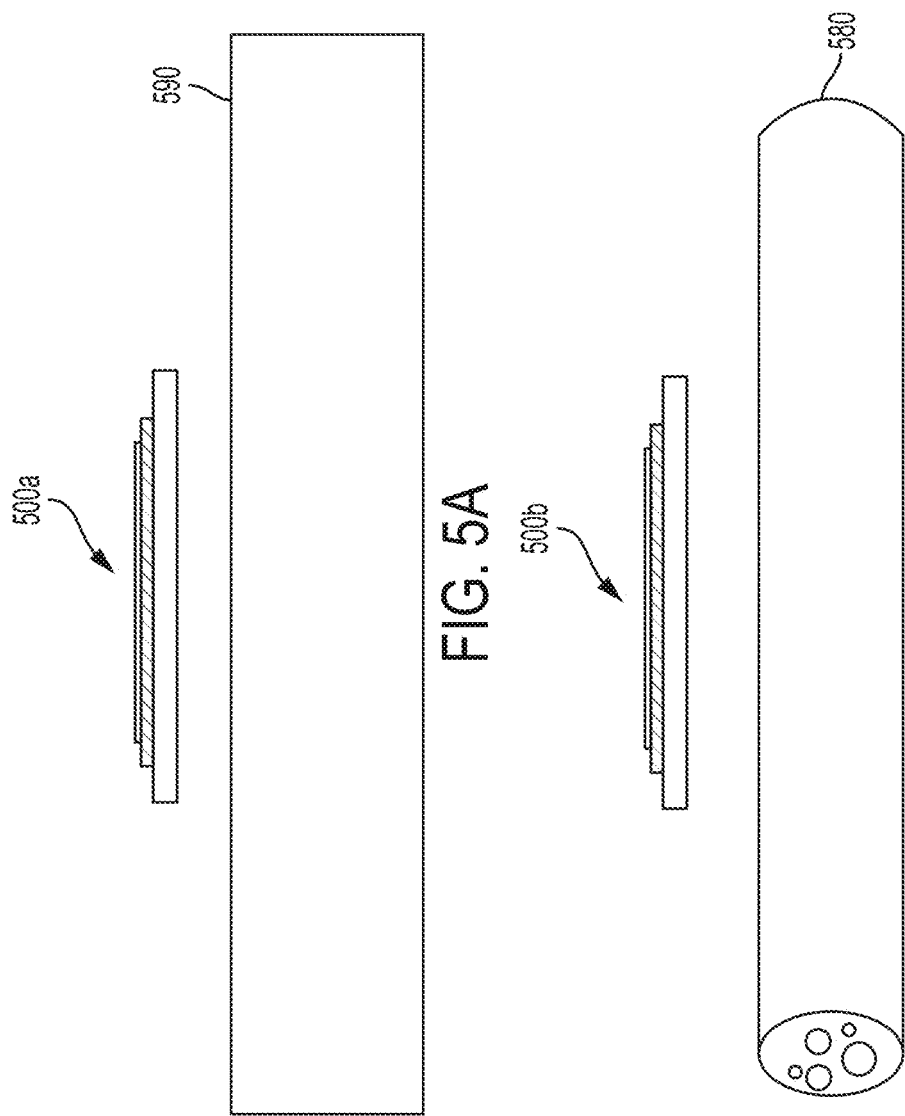

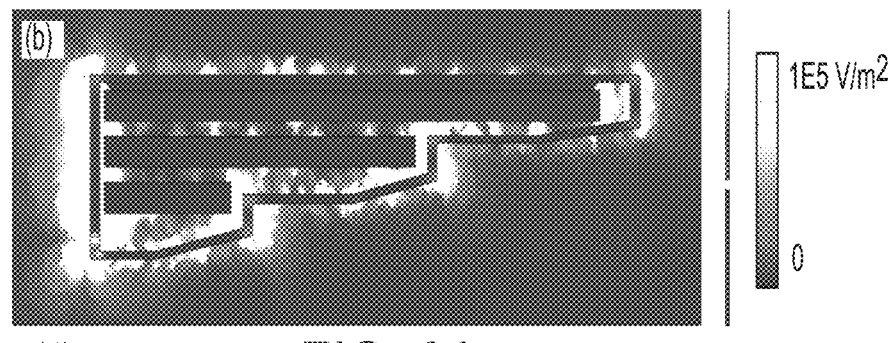
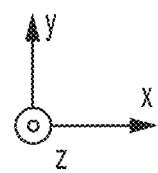
FIG. 6A
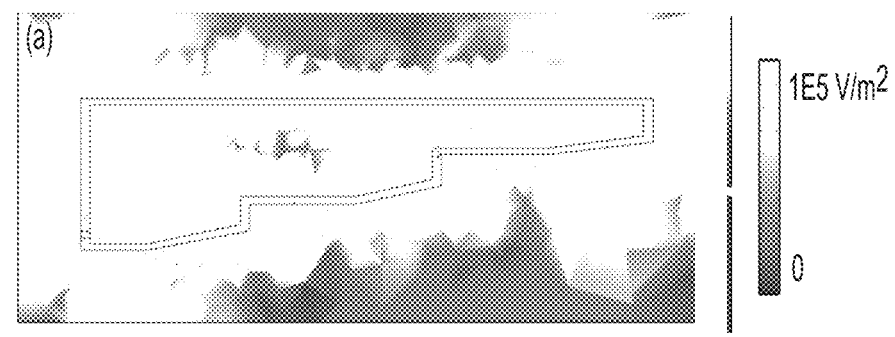
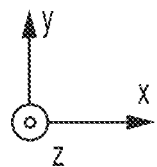
FIG. 6B

MICRO COILS SUITABLE FOR MAGNETIC NEURAL STIMULATION

STATEMENT REGARDING FEDERALLY SPONSORED RESEARCH AND DEVELOPMENT

This invention was made with Government support under government contract number 1U01NS099700-01 awarded by the NIH. The Government has certain rights in this invention.

TECHNICAL FIELD

This disclosure relates generally to devices, systems, and methods for magnetic stimulation of neurons.

BACKGROUND

Neuromodulation is an evolving therapy that can involve various types of electromagnetic stimuli including the application of a strong magnetic field or a small electric current to nerve structures.

SUMMARY

Some embodiments are directed to an implantable magnetic neurostimulation probe. The magnetic neurostimulation probe includes at least one electrical conductor disposed on at least one substrate and arranged in at least one planar loop. At least one planar magnetic core comprising a magnetic material is disposed on the substrate and within the planar loop. A biocompatible coating is disposed over the substrate, the electrically conductive trace, and the magnetic core.

In accordance with some embodiments, a method involves applying an electrical current of about 10 mA to 60 mA to a magnetic probe having least one electrical conductor. The electrical conductor is disposed on the substrate and is arranged as at least one planar loop. At least one magnetic core comprising a magnetic material is disposed on the substrate and within the planar loop. In response to the applied electrical current, the magnetic probe produces an excitation volume having a boundary with a radius of about 50 μm such that an electric field gradient generated by the magnetic probe is greater than 11000 V/m$^2$ within the boundary and is less than 11000 V/m$^2$ at and beyond the boundary.

Some embodiments are directed to a system that comprises an implantable magnetic neurostimulation probe and an energizer electrically coupled to the probe. The implantable magnetic neurostimulation includes at least one substrate; at least one electrical conductor disposed on the substrate and arranged as at least one planar loop; at least one planar magnetic core comprising a magnetic material disposed on the substrate and within the planar loop; and a biocompatible coating is disposed over the substrate, coil, and magnetic core. The energizer is configured to apply the electrical current through the electrical conductor.

In accordance with some embodiments and magnetic probe includes at least one electrical conductor disposed on a substrate and arranged as at least one planar loop. At least one planar magnetic core comprising a magnetic material is disposed on the substrate and within the planar loop. When energized by an electric current through the loop, the probe is configured to produce an excitation volume having an boundary with a radius of about 50 μm such that an electric field gradient generated by the probe is greater than 11000 V/m$^2$ within the boundary and is less than 11000 V/m$^2$ at and beyond the boundary.

BRIEF DESCRIPTION OF THE DRAWINGS

FIG. 5A illustrates a magnetic probe used in the implementation of a magnetic force microscope in accordance with some embodiments;

FIG. 5B illustrates a neural probe used for neurostimulation in accordance with some embodiments;

FIG. 6A shows a simulation of the electric field gradient dEx/dx produced by a magnetic probe as in FIG. 2;

FIG. 6B shows a comparative simulation of the electric field gradient dEx/dx produced by a magnetic probe as in FIG. 2 but without the magnetic cores;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1A:
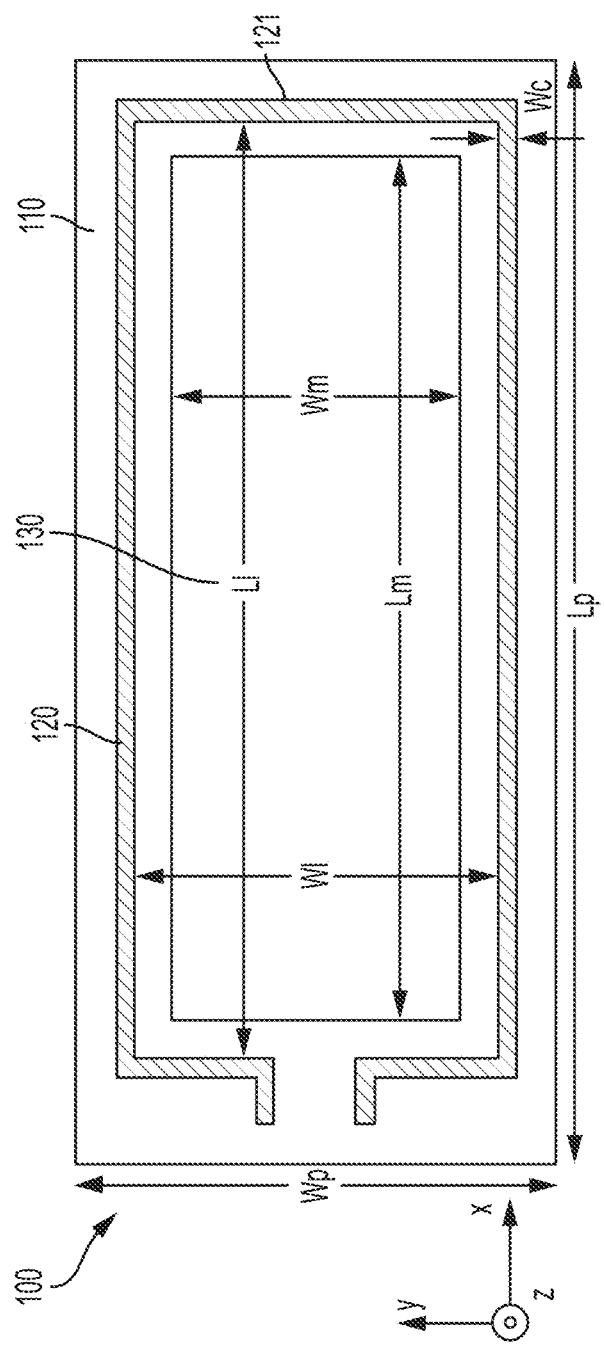
FIGS. 1A and 1B respectively illustrate top and side views of a magnetic probe in accordance with some embodiments.

Neural stimulation has the potential to treat a large number of neurological disorders. However, it can be challenging to provide effective stimulation that activates the targeted neurons without concurrently activating nearby neurons that are not targeted. Unintentional activation of non-targeted neurons leads to the spread of activation beyond the target area with undesirable or unknown results.

When magnetically stimulated, neurons are activated by the spatial gradient of the electric field produced by an energized a magnetic coil. Magnetic coils suitable for neurostimulation can produce an electric field gradient that is sufficient to activate neurons, e.g., about 11000 V/m$^2$, within an activation volume which extends outwardly in three dimensions from the location of the magnetic coil. The activation volume has a radius that defines the activation boundary of the spatial gradient of the electric field. The spatial gradient of the electric field is sufficient to activate neurons within the activation volume but is insufficient to activate neurons at the boundary or outside the boundary of the activation volume.

Magnetic stimulation of neurons using implanted magnetic probes potentially has several advantages when compared to conventional electrical stimulation of neurons. The electric fields generated by implanted micro coils can be spatially asymmetrical and therefore may be more amenable to selective activation of targeted neurons than neurostimulation using conventional neuroelectrical stimulation. Furthermore, in comparison to conventional neural stimulation by electrical probes, magnetic fields more readily pass through biologic materials without substantial attenuation. Magnetic stimulation coils do not need to be placed in direct contact with the targeted neurons and can be encapsulated in biocompatible materials.

Embodiments disclosed herein involve magnetic probes suitable for use in neural stimulation as well as other implementations. The magnetic probes incorporate micro coils which can have any suitable shape or configuration, e.g., planar or three dimensional (3D) coils. In some embodiments, the magnetic probes incorporate micro coils in the form of planar loops disposed on a substrate with high magnetic permeability cores disposed at least partially within the loops. The magnetic cores allow the planar loops to be energized by low currents that produce high electric field gradients which do not extend beyond relatively small activation volumes. The smaller activation volumes produced by the disclosed magnetic probes are useful to selectively target specific locations without affecting or minimally affecting other locations. For example, when the disclosed magnetic probes are used for magnetic neural stimulation, the activation volumes allow for activation of targeted neurons without activation of nearby non-targeted neurons. According to various implementations, the disclosed magnetic probes can produce electric field gradients greater than $1.1 \times 10^4$ V/m$^2$ within the activation volume, thus providing a spatial electric field gradient that is sufficient for the stimulation of biological nerves. These electric field gradients can be produced using an energizing current through the micro coil on the order of about 50 mA at a voltage of about 1 V.

Figure 1B:
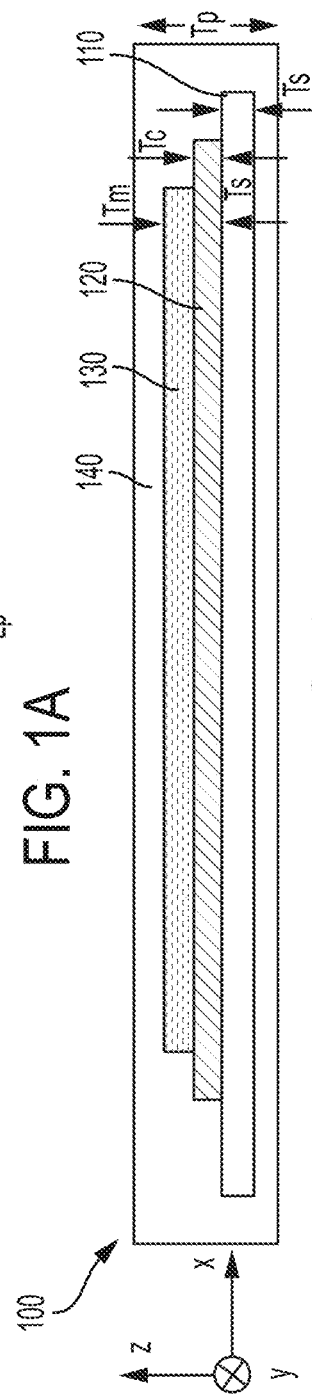

FIGS. 1A and 1B are conceptual diagrams that illustrate top (FIG. 1A) and side (FIG. 1B) views of a magnetic probe 100 in accordance with some embodiments. The magnetic probe 100 comprises a substrate 110 having at least one electrically conductor 120 disposed on the substrate 110 and arranged as at least one electrically continuous planar loop 121. A planar magnetic core 130 comprising a magnetic material is disposed on the substrate 110 and at least partially within the planar loop 121. As shown in FIGS. 1A and 1B, the planar magnetic core 130 and the electrical conductor 120 can be coplanar, wherein both are disposed on the same surface of the substrate 110. For medical applications, the magnetic probe 100 may be encapsulated within a suitable biocompatible coating 140 which is disposed over the substrate 110, the electrical conductor 120, and the magnetic core 130.

The substrate 110 may be flat and/or rigid and may comprise materials such as silicon, germanium, sapphire, quartz and/or fused silica, among other materials. According to some implementations, the electrical conductor 120 can be an electrically conductive trace deposited onto the substrate 110. The electrical conductor 120 can comprise various metals, including gold, silver, copper, aluminum, nickel, platinum and/or alloys thereof, for example. The magnetic core 130 may have magnetization change per cm$^3$ mol$^{-1}$ in a range of about 10 to 2000 G, for example. Suitable materials for the magnetic core 130 include ferromagnetic materials, including iron, cobalt, nickel, and/or alloys thereof. In additional examples, some ceramics, such as yttrium-based ceramics could be used. The substrate 110, electrical conductor 120, and magnetic core 130 may be at least partially or fully encapsulated by an encapsulant 140, e.g., a hermetic encapsulant and/or a biocompatible encapsulant. Suitable encapsulants include polyimide or silicon oxynitride ($SiON_x$).

The magnetic probe 100 may have an overall length, Lp, in a range of about 2 mm to 5 mm, an overall width, Wp, in a range of 50 μm to 200 μm, and an overall probe thickness, Tp, (which includes the thickness of the substrate, electrical conductor, magnetic core, and encapsulant) in a range of about 55 μm to about 510 μm.

The substrate 110 can have a thickness, Ts, in a range of about 25 μm to 500 μm.

The electrical conductor 120 may have a width, Wc, in a range of about 1 μm to about 20 μm and a thickness, Tc, in a range of about 1 μm to about 10 μm. The electrical conductor 120 that forms the loop can have an overall length, Lc, between about 5 mm and about 20 mm.

The loop 121 may be rectangular, as shown in FIG. 1A or may have any suitable shape, including planar, three dimensional coils, etc. The loop 121 (or each loop in the probe) may have a maximum length, Ll, between about 2 mm and about 5 mm and a maximum width, Wl, between about 30 μm and about 150 μm.

The magnetic core 130 may have a generally rectangular shape as depicted in FIG. 1A, or may have any other suitable shape such that the magnetic core is at least partially encircled by the loop 121. For example, the magnetic core 130 may have a maximum length, Lc, between about 2 mm and 5 mm and a maximum width, Wc, between about 30 μm and about 150 μm, and a thickness, Tm, between about 1 μm and about 10 μm.

In some embodiments, the loop may have a more complex shape than the simple loop illustrated in FIGS. 1A and 1B.

According to some embodiments, multiple magnetic cores may be disposed within a single loop of the electrical conductor, as illustrated in FIG. 2. FIG. 2 provides a top view of a magnetic probe 200 that includes an electrical conductor 220 disposed on a substrate 210 and forming a planar loop 221. Multiple magnetic cores 231, 232, 233 are at least partially encircled by the loop 221. In the embodiment shown in FIG. 2, the planar loop 221 has a stair-step or sawtooth profile along edge 250 that generally conforms to the different lengths of the magnetic cores 231, 232, 233. In some embodiments, additional edges may also have the sawtooth profile. Although three magnetic cores are shown in FIG. 2, any suitable number of magnetic cores may be at least partially encircled within the loop 221. Each of the magnetic cores 231, 232, 233 may be made of the same magnetic material in some embodiments. Alternatively, the magnetic material that makes up at least one of the magnetic cores 231, 232, 233 may differ from the magnetic material that makes up another of the magnetic cores. The magnetic cores 231, 232, 233 may have the same geometry, e.g., same shape, same area, same thickness. Alternatively, as illustrated in FIG. 2, one or more of the magnetic cores 231, 232, 233 may have geometry that is different from the geometry of other magnetic cores. In the embodiment illustrated in FIG. 2, magnetic core 231 is longer and has a larger surface area than magnetic cores 232 and 233; and magnetic core 232 is longer and has a larger surface than magnetic core 233.

The magnetic cores 231, 232, 233 are disposed within respective sections 221-1, 221-2, 221-3 of the magnetic loop 221. Magnetic core 231 is disposed within loop section 221-1; magnetic core 232 is disposed within loop section 221-2; and magnetic core 233 is disposed within loop section 221-3.

The magnetic probe 200 may have an overall length, in a range of about 2 mm to 5 mm, an overall width in a range of 50 μm to 200 μm, and a thickness in a range of about 2 μm to 10 μm. For example, the substrate 210 can have a thickness in a range of about 25 μm to 500 μm.

The electrical conductor 220 may have a width in a range of about 1 μm to 20 μm and a thickness in a range of about 1 μm to about 10 μm. The first loop section 221-1 may have a maximum length, L11, between about 2 mm and 5 mm and a maximum width, W11, between about 30 μm and 150 μm.

According to some embodiments, the second loop section, 221-2, may have a length, L12 that is about 50 to 75% of the length, L11, of the first loop section 221-1. The third loop section, 221-3, may have a length, L13 that is about 50 to 75% of the length, L12, of the second loop section 221-2. The widths, W11, W12, W13 of the first, second and third loop sections 221-1, 221-2, 221-3 can be about the same in some embodiments.

By virtue of the step-like pattern in the sawtooth profile, the different locations of the terminated tips 251a, 252a, 253a of the loop 221 give control over the transverse field gradient (in the x-y plane) depending upon the insertion into the biological tissue. The sawtooth shape shown in FIG. 2A permits the control of the electric field gradients along the depth of insertion. The tips of the sawtooth coils provide for control of electric field gradients in the transverse direction.

Figure 2A:
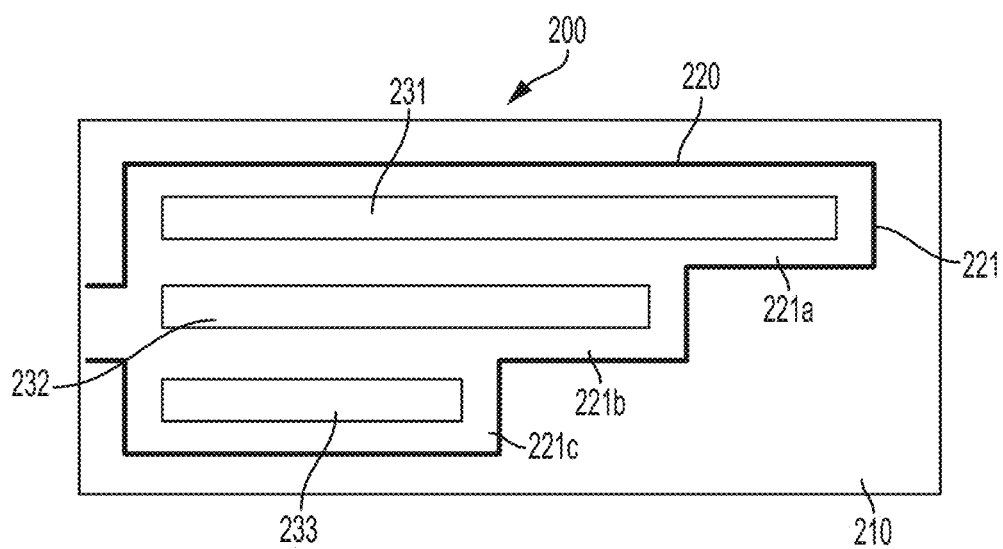
FIG. 2A illustrates a magnetic probe having multiple magnetic cores disposed within a single loop having a sawtooth profile in accordance with some embodiments.
Figure 2B:
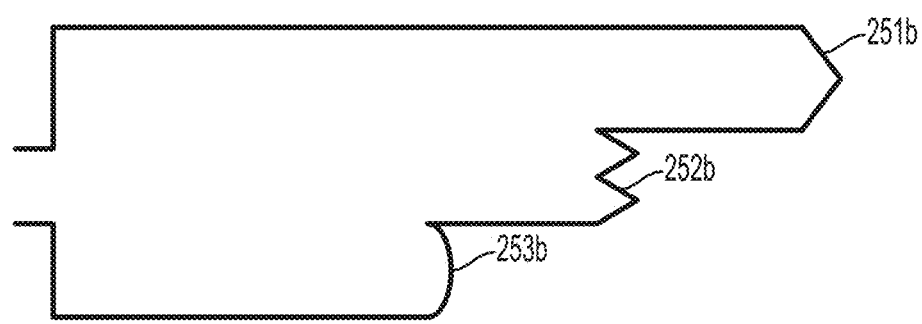
FIG. 2B illustrates some different loop section tip configurations in accordance with some embodiments.

In FIG. 2A, each of the tips 251a, 252a, 253a is straight and extends along they axis However, the tips of the loop sections 221a, 221b, 221c may have other shapes as shown in FIG. 2B. FIG. 2B illustrates a V-shaped tip 251b, a U-shaped tip 253b, and a W-shaped tip 252b. As illustrated in FIG. 2B, the tips of a magnetic probe need not be terminated identically. The shape of the tips permits substantial differences in the transverse field gradients and allows the transverse gradients to be shaped according to the particular application. Depending upon the coil shape, the anisotropy of the field-gradient as well as the field strength can be varied. This permits selective directional excitation of neurons.

A magnetic probe may include multiple magnetic cores disposed within multiple planar loops. In some embodiments, the multiple loops may be formed using a single electrically continuous electrical conductor, e.g., arranged in a spiral comprising multiple concentric loops. In some embodiments, the loops may be formed using multiple separate electrical conductors, e.g., multiple electrically separate concentric loops.

Figure 3:
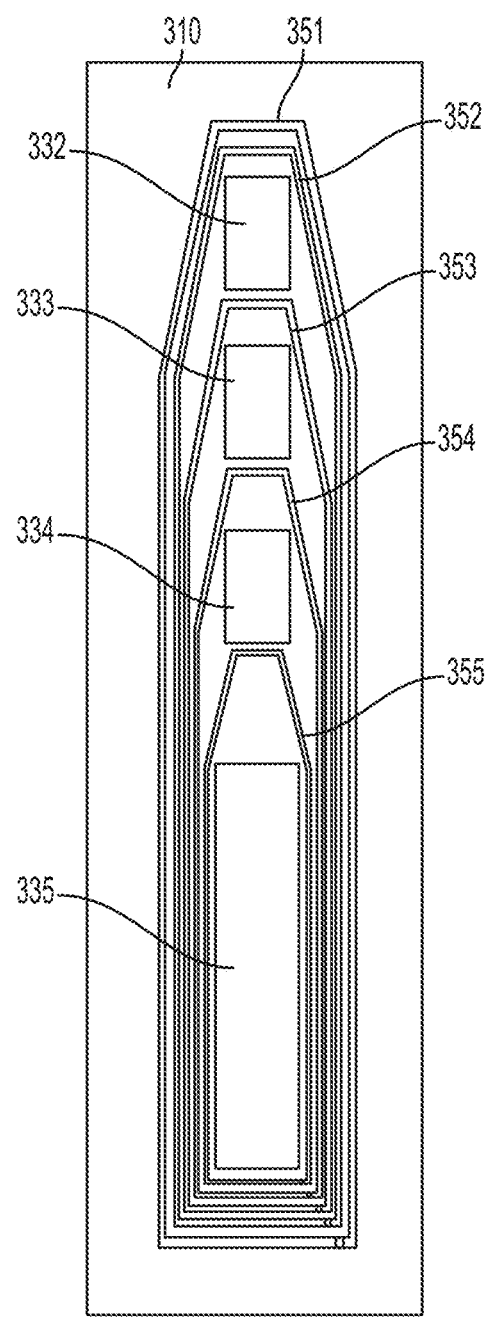
FIG. 3 is a diagram of a magnetic probe comprising multiple magnetic cores disposed within multiple concentric planar loops according to some embodiments.

An example of a magnetic probe 300 having multiple concentric cores 332, 333, 334, 335 and multiple loops 351, 352, 353, 354, 355 is provided in FIG. 3. In the embodiment illustrated by FIG. 3, each core 332, 333, 334, 335 is at least partially enclosed within at least one loop 351, 352, 353, 354, 355. At least some of the cores 333, 334, 335 may be at least partially enclosed within multiple loops 351 353, 354, 355 while other cores 332 may be disposed within fewer loops 351, 352 or within only one loop. In the example shown in FIG. 3, loops 351 and 352 at least partially encloses all the magnetic cores 332, 333, 334, 335; loop 353 at least partially encloses cores 333, 334, 335 and core 332 is disposed outside loop 353; loop 354 at least partially encloses cores 334 and 335 cores 332 and 333 are disposed outside loop 354; loop 355 at least partially encloses core 335 and cores 332, 333, and 334 are disposed outside loop 355. As previously discussed, the geometry of at least one of the magnetic cores may be the same or may differ from the geometry of other magnetic cores. The multiple magnetic cores may have other characteristics that differ from core to core. For example, the magnetic cores may have the same or different magnetic permeability, material composition, etc.

The magnetic probe 300 may have an overall length, in a range of about 2 mm to 5 mm, an overall width in a range of 50 μm to 200 μm, and an overall thickness (including the substrate, electrical conductor, core, and encapsulant) in a range of about 51 μm to about 501 μm. The electrical conductors of loops 351-355 may have a width in a range of about 1 μm to 20 μm and a thickness in a range of about 1 μm to about 10 μm.

Loop 351 may have a maximum length, L11 between about 2 mm and 5 mm and a maximum width, W11, between about 30 μm and 150 μm.

According to some embodiments, the second loop, 352 may have a length that is about 75 to 90% of the length of the length of the first loop 351; loop 353 may have a length that is about 50 to 75%% of the length of the loop 352; loop 354 may have a length that is about 50 to 75%% of the length of loop 353; and loop 355 may have a length that is about 50 to 75%% of the length of loop. In some embodiments, the surface area of some of the cores can be the same, e.g., cores 332, 333, 334 in FIG. 3 and the surface area of one or more of the cores can differ from the surface area of another core. For example, core 335 is wider and longer than cores 332, 333, 334.

In the configuration shown in FIG. 3, there are a few distinct degrees of freedom that can be controlled, including magnetic core size, proximity of magnetic core to the loop, and tips of the loops, to name a few. By adjusting the parameters independent of each other, one can tailor the electric field gradient to customizable configurations with the intentional narrowing down of the spread of the field lines. By adjusting these and/or other parameters, the control of the electric field gradient can be enhanced.

Figure 4A:
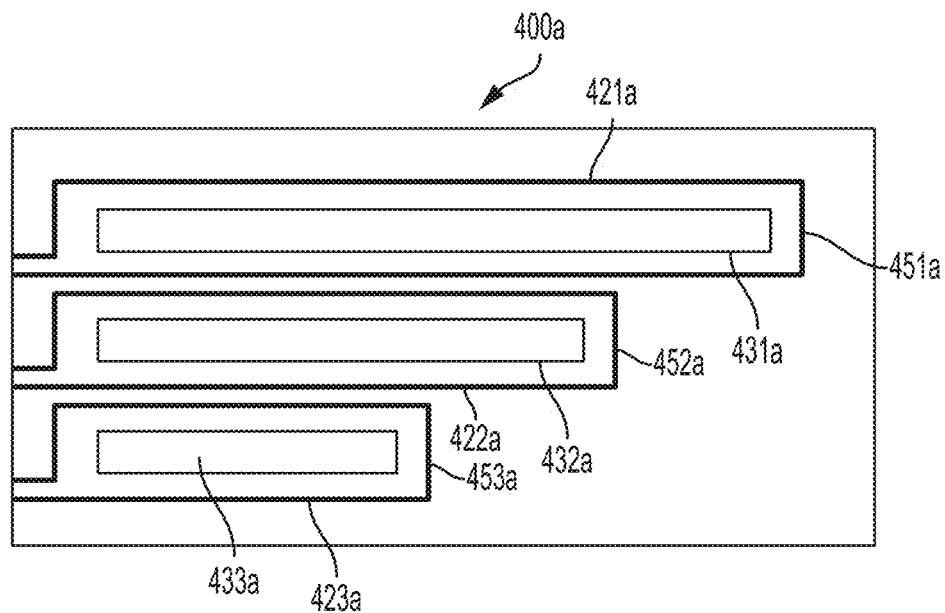
FIG. 4A is a top view of a magnetic probe comprising multiple coplanar electrically isolated loops according to some embodiments.
Figure 4B:
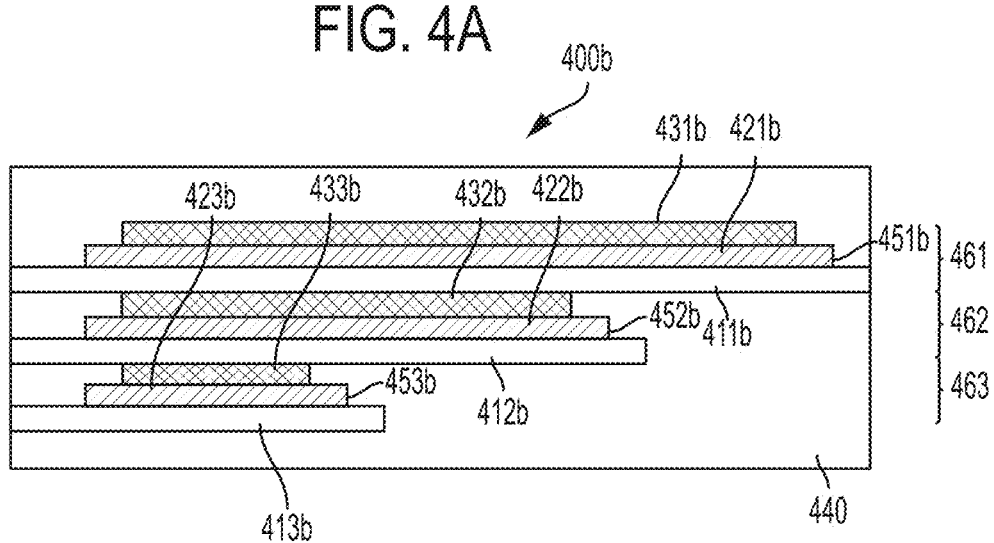
FIG. 4B is a side view of a magnetic probe comprising multiple coplanar electrically isolated loops stacked vertically according to some embodiments.

According to some embodiments, a magnetic probe can include multiple electrically non-continuous loops as illustrated by FIGS. 4A and 4B. FIG. 4A shows a top view of a magnetic probe 400a comprising multiple loops 451a, 452a, 453a. Each loop 451a, 452a, 453a is respectively formed by an electrical conductor 421a, 422a, 423a which is electrically isolated from the other electrical conductors 421a, 422a, 423a. Each of the loops 451a, 452a, 453a can be energized concurrently or at different times. Each of the loops 451a, 452a, 453a can be energized by the same current value. Alternatively, at least one of the loops can be energized by a current value that is different from the current value used to energize another of the loops.

The loops 451a, 452a, 453a may differ in geometry, e.g., as shown in FIG. 4A. In the illustrated embodiment, loop 451a encloses a larger surface area than loops 452a and 453a; and loop 452a encloses a larger surface area than loop 453a. Accordingly, the electrical conductor 421a that forms loop 451a is longer than the electrical conductors 422a and 423a that respectively form loops 452a and 453a. The electrical conductors 421a, 422a, 423a of the different loops 451a, 452a, 453a may be made of the same electrically conductive material, or the electrically conductive material may vary from loop to loop in some embodiments.

Magnetic core 431a is at least partially enclosed by loop 451a; magnetic core 432a is at least partially enclosed by loop 452a; and magnetic core 433a is at least partially enclosed by loop 453a. In the magnetic probe 400a, each core 431a, 432a, 433a is enclosed by only one of the loops 421a, 422a, 423a. As previously discussed, the geometry, surface area, shape, material, thickness, etc. of the magnetic cores may vary from core to core in some embodiments, Alternatively, at least some of these characteristics may not vary from core to core.

FIG. 4A shows single loops 451a, 452a, 453a wherein each loop 451a, 452a, 453a at least partially encloses one magnetic core 431a, 432a, 433a. Alternatively, multiple loops of a single continuous electrical conductor, e.g., multiple spiral loops, or multiple concentric loops of separate electrical conductors loops may be used as previously discussed in connection with FIG. 3, for example. Alternatively, each single loop may at least partially enclose multiple magnetic cores, for example, as previously discussed in connection with FIG. 2. An encapsulant (not shown in FIG. 4A can be disposed over the loops 451a, 452a, 453a and magnetic cores 431a, 432a, 433a.

FIG. 4B provides a side view of a magnetic probe 400b that includes multiple electrically isolated electrically conductive loops 451b, 452b, 453b. In this example, the electrical conductors 421b, 422b, 423b forming the loops 451b, 452b, 453b are disposed respectively on separate substrates 411b, 412b, 413b. Magnetic cores 431b, 432b, 433b are disposed respectively within loops 451b, 452b, 453b.

As illustrated in FIG. 4B, electrical conductor 421b and magnetic core 431b are disposed on the same surface of substrate 411b. Electrical conductor 421b forms loop 451b which at least partially encloses magnetic core 431b. Electrical conductor 422b and magnetic core 432b are disposed on substrate 412b. The electrical conductor 422b and magnetic core 432b are disposed on the same surface of substrate 412b. Electrical conductor 422b forms loop 452b which at least partially encloses magnetic core 432b. Electrical conductor 423b and magnetic core 433b are disposed on the same surface of substrate 413b. Electrical conductor 423b forms loop 453b which at least partially encloses magnetic core 433b.

Substrate, 411b, loop 451b, and core 431b form a first portion 461 of the magnetic probe 400b; substrate, 412b, loop 452b, and core 432b form a second portion 462 of the magnetic probe 400b; and substrate, 413b, loop 453b, and core 433b form a third portion 463 of the magnetic probe 400b. An encapsulant 440 can be disposed over each of the first, second, and third portions 461, 462, 463.

According to some embodiments, each of the first, second, and third portions 461, 462, 463 may comprise a single core within a single loop as described in connection with FIGS. 1A and 1B. According to some embodiments, each of the first, second, and third portions 461, 462, 463 may comprise multiple cores within a single loop as described in connection with FIG. 2. According to some embodiments, each of the first, second, and third portions 461, 462, 463 may comprise multiple cores disposed respectively within multiple loops as described in connection with FIG. 3. Each of the first, second, and third portions 461, 462, 463 may comprise various combinations of multiple cores disposed respectively within multiple loops, single cores disposed within single loops, and/or multiple cores disposed within single loops.

FIGS. 5A and 5B illustrate two technical applications for the disclosed magnetic probe. In the technical application shown in FIG. 5A, the probe 500a is used to implement a magnetic force microscope. In this implementation, the magnetic probe 500a is moved over the surface of a magnetic sample 590. As the probe 500a is scanned over the surface, the probe converts the magnetic fields at the surface of the sample into currents that are induced in the loop. The induced current in the loop(s) of the probe can be used to provide information about the magnetic structure of the sample surface.

In the technical application shown in FIG. 5B, the probe 500b is used to stimulate neurons of a nerve bundle. The probe 500b, placed proximate to the nerve bundle 580, is energized by supplying an electrical current through the one or more loops of the probe 500b. The electrical current is supplied from an external source (not shown in FIG. 5B) through the loop(s) and produces an electric field gradient sufficient to activate the targeted nerve fibers within the nerve bundle.

This design of the disclosed magnetic probe enables excitation at different locations within the spatial boundaries of a structure depending on the amplitude of the current injection in the loops. FIGS. 6A through 8B show a comparison between the performance of a magnetic probe as generally illustrated in FIG. 2 (referred to herein as the sawtooth design) with and without the high permeability magnetic cores. The sawtooth geometry supports transverse (dEz/dz) control over the excitation volume produced by the magnetic probe.

The direct way to obtain a larger electric field gradient is to use a larger AC current excitation. However, one of the consequences of simply increasing the current in the micro coils is that the volume of excitation also increases. For example, increasing currents through a 10 μm wide Cu loop from 1 mA to 100 mA, generates an increase in a volume of excitation with radius>150 μm. This can lead to stimulation of non-targeted regions. However, a micro-coil geometry with high permeability cores can still maintain a small excitation volume (within a radius of about 50 μm) with about 50 mA currents at electric field gradients of greater than 11000 V/m$^2$ or even about 10$^7$ V/m$^2$.

Figure 7A:
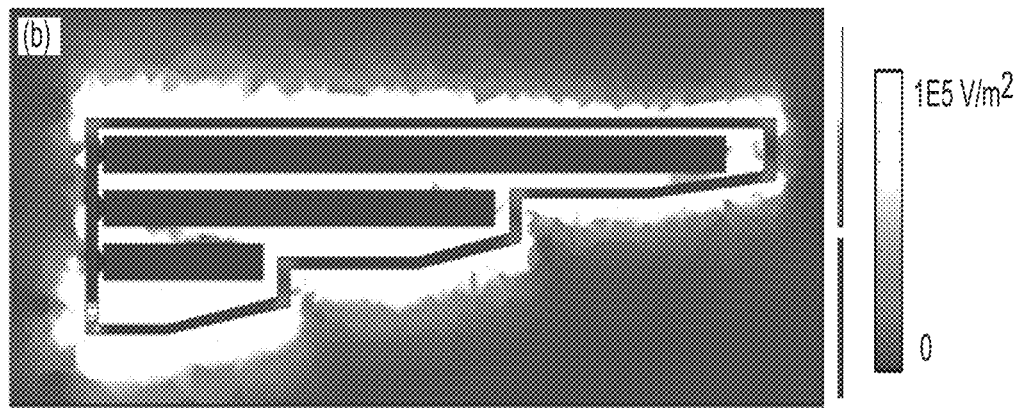
FIG. 7A shows a simulation of the electric field gradient dEy/dy produced by a magnetic probe as in FIG. 2.
Figure 7B:
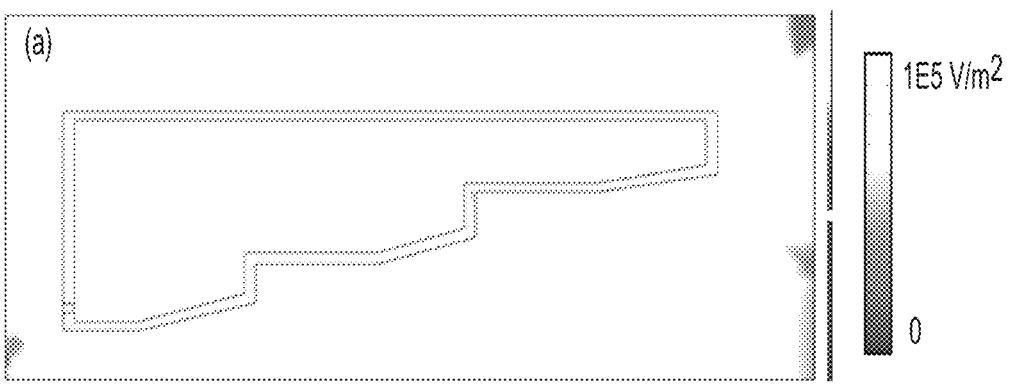
FIG. 7B shows a comparative simulation of the electric field gradient dEy/dy produced by a magnetic probe as in FIG. 2 but without the magnetic cores.
Figure 8A:
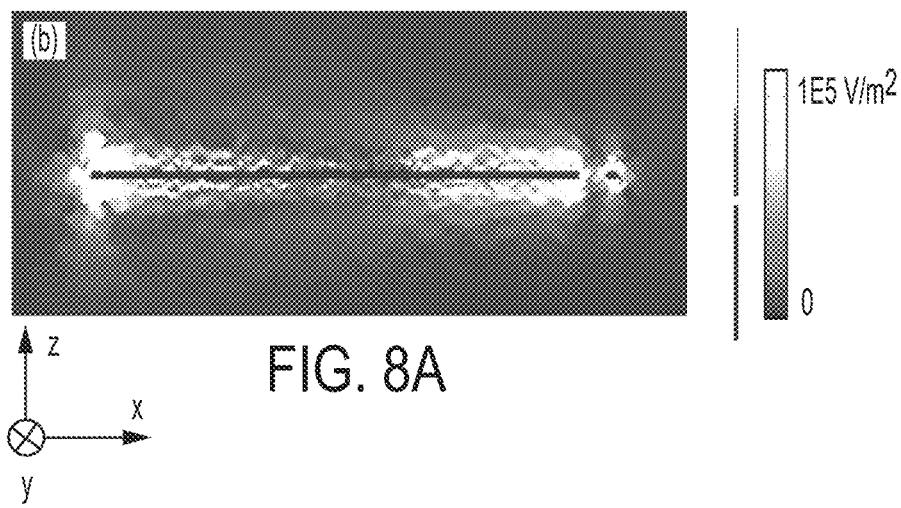
FIG. 8A shows a simulation of the electric field gradient dEz/dz produced by a magnetic probe as in FIG. 2.
Figure 8B:
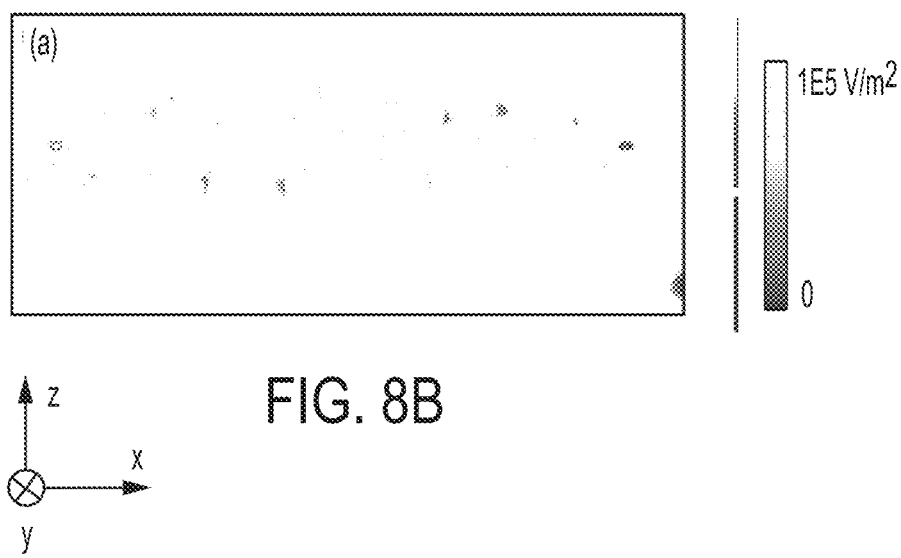
FIG. 8B shows a comparative simulation of the electric field gradient dEz/dz produced by a magnetic probe as in FIG. 2 but without the magnetic cores.

FIG. 6A shows a simulation of the electric field gradient, dEx/dx, produced by a magnetic probe as in FIG. 2 when a current of 50 mA is supplied through the loop. For comparison, FIG. 6B shows a simulation of the electric field gradient, dEx/dx, produced by a magnetic probe as in FIG. 2 but without the magnetic cores when a current of 50 mA is supplied through the loop. FIG. 7A shows a simulation of the electric field gradient, dEy/dy, produced by a magnetic probe as in FIG. 2 when a current of 50 mA is supplied through the loop. For comparison, FIG. 7B shows a simulation of the electric field gradient, dEy/dy, produced by a magnetic probe as in FIG. 2 but without the magnetic cores when a current of 50 mA is supplied through the loop. FIG. 8A shows a simulation of the electric field gradient, dEz/dz, produced by a magnetic probe as in FIG. 2 when a current of 50 mA is supplied through the loop. For comparison, FIG. 8B shows a simulation of the electric field gradient, dEz/dz, produced by a magnetic probe as in FIG. 2 but without the magnetic cores when a current of 50 mA is supplied through the loop.

In the example illustrated in FIGS. 6A, 7A, and 8A, the magnetic probes having the magnetic cores produce an electric field gradient greater than about $1.1 \times 10^4$ V/m$^2$ and/or up to about $10^6$ V/m$^2$ within an activation volume having a radius of about 30 μm. The electric field gradient is less than $1.1 \times 10^4$ V/m$^2$ at the boundary of the activation volume. In the comparative example, the activation volume of the magnetic probe without the magnetic cores as indicated by FIGS. 6B, 7B and 8B has a radius greater than about 100 μm. Incorporating multiple magnetic cores into the loop of a magnetic probe can reduce the volume of the activation volume for neural stimulation by more than about 20 to about 70%. For example, incorporating multiple magnetic cores into a magnetic probe as in the embodiments illustrated herein can reduce the volume of the activation volume for neural stimulation by about 60%.

Figure 9:
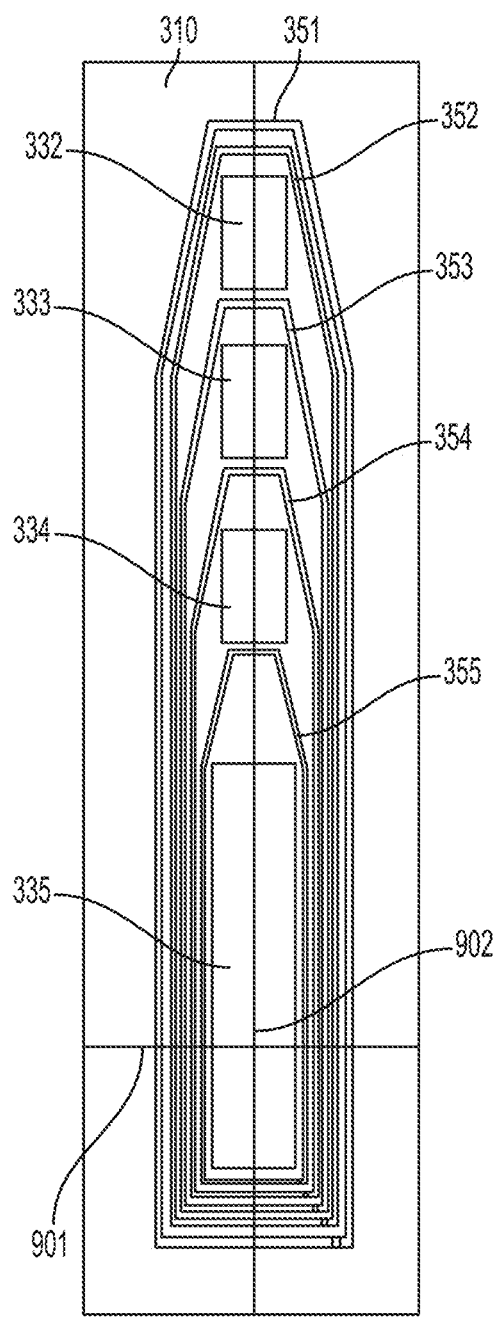
FIG. 9 shows the neural probe 300 of FIG. 3 with lateral and longitudinal cross section lines.
Figure 10A:
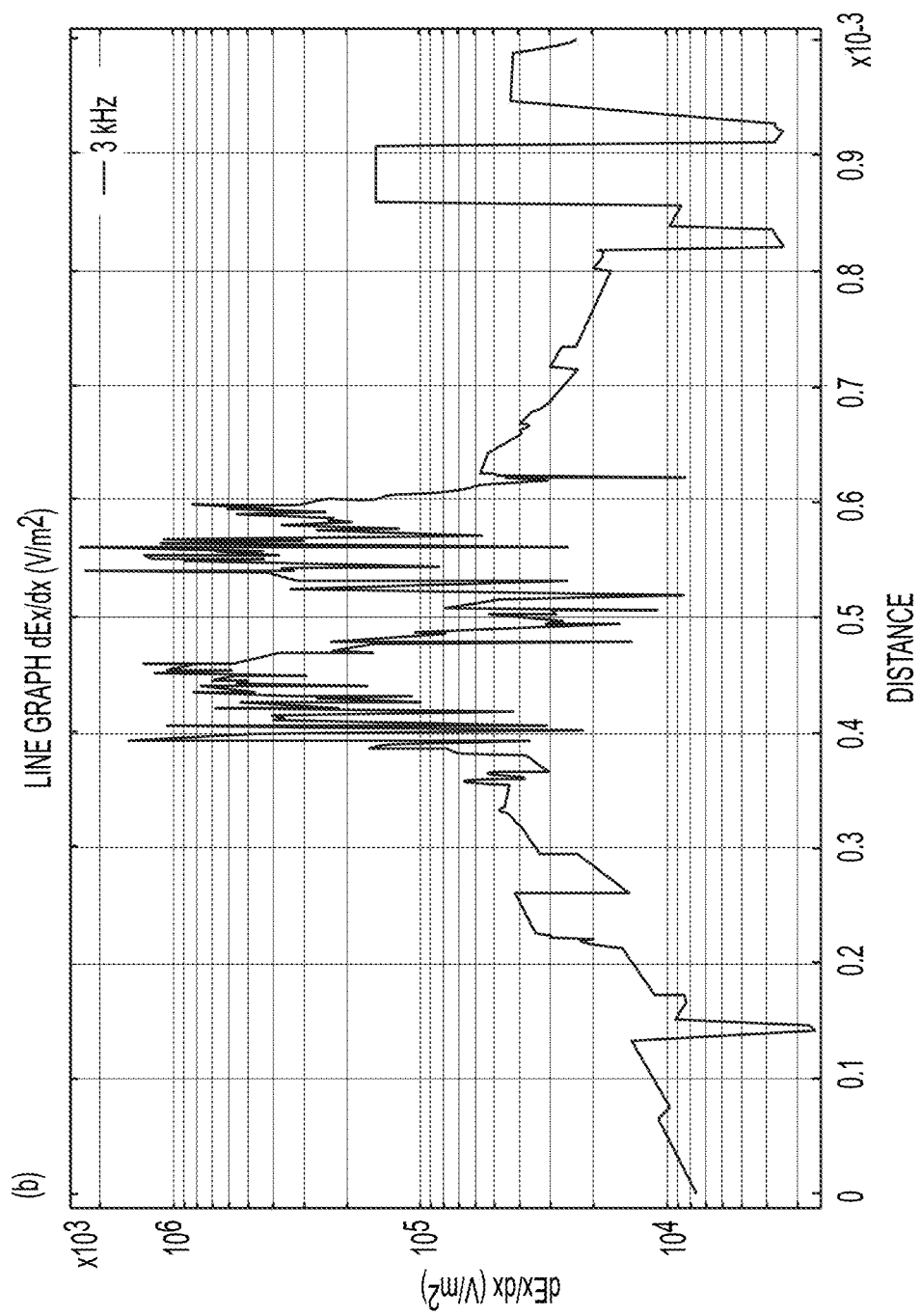
FIG. 10A is a graph of the simulated electric field gradient along the lateral cross section line.
Figure 10B:
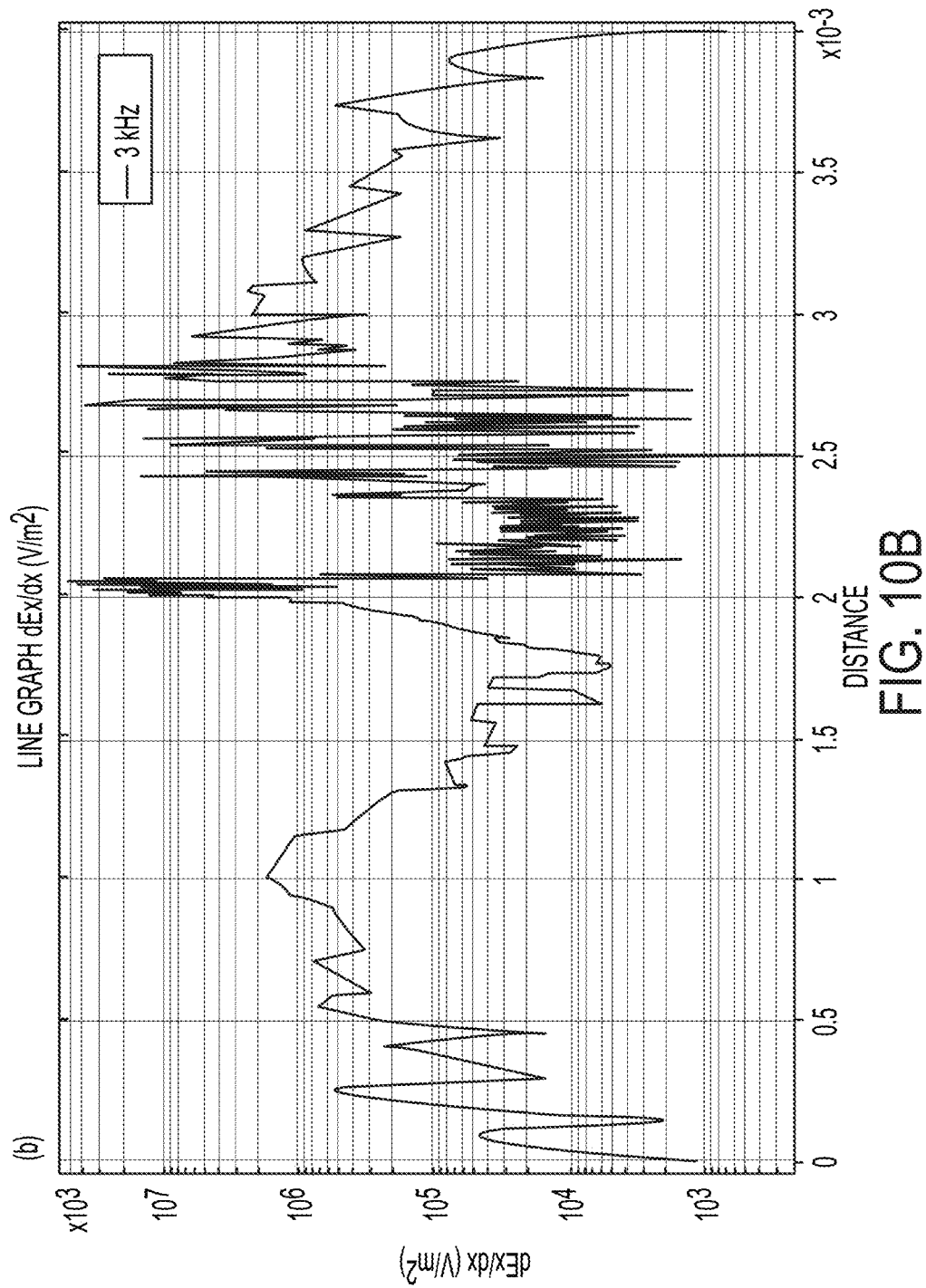
FIG. 10B is a graph of the simulated electric field gradient along the longitudinal cross section line.

Simulations were also performed for the multiple loop neural probe shown in FIG. 3. FIG. 9 shows the neural probe 300 of FIG. 3. FIG. 10A shows the line cross section of the electric field gradient along line 901 in FIG. 9. FIG. 10A indicates that the electric field gradient along the cross-section is maximal near the regions proximate to the coils (within a distance of about 75 μm from the central axis) and with a value of about $10^6$ V/m$^2$. Line 901 in FIG. 10A represents the path along which the cross-section was taken in this simulation. In FIG. 10A, 0 on the x-axis corresponds the the leftmost point of line 901 in FIG. 9 and $10^{-3}$ on the x-axis corresponds to the rightmost point of line 901. FIG. 10B shows the line cross section of the electric field gradient along line 902 in FIG. 9. In FIG. 10B, 0 on the x-axis corresponds the the lowest point of line 902 in FIG. 9 and $4 \times 10^{-3}$ on the x-axis corresponds to the topmost point of line 902.

The width of the magnetic probe in this simulated example is 200 μm. The magnetic probe 300 includes five electrically isolated concentric loops 351-355 having five different total lengths. The loops 351-355 at least partially enclose a different number of cores 332-335, from one core to four cores. The width of the loops 351-355 can be modified to obtain different decay depths away from the coils 332-335 of the electric field gradient at or above the gradient threshold value of 11000 V/m$^2$. The edges of the loops are regions where there is a strong discontinuity in the dielectric constant of the materials across the interface. A wider loop spreads the field lines more than a narrower loop. However a narrower loop would also increase the resistance. Therefore an interplay between the current requirements and the field-narrowing requirements can be used to ascertain a loop width suitable for a particular application.

In this example, as shown in FIGS. 10A and 10B, the electric field gradient is above the threshold for neural activation up to a distance of about 125 μm away from the coils 331-335. In this particular example, the threshold for neural activation corresponds to an electric field gradient larger than 11000 V/m$^2$. However, in other scenarios, the threshold may be different depending on the neuron being excited. There is a narrow region of width of about 75 μm proximate to the coils that exhibits high electric field gradients of the order of $10^6$ V/m$^2$. FIG. 10B shows the electric field gradient along the longitudinal cross section. Line 902 is the path along with the longitudinal electric field gradient has been evaluated. Electric field gradients of up to $10^7$ V/m$^2$ can be seen in regions as small as 20 μm.

The reason for such high electric-field gradients can be understood by considering that this design is similar to a 2D solenoid with a high permeability core. With the "length" of the solenoid approaching a very small number (2 μm in this case, or the corresponding thickness of the trace), when the number of loops around the core is increased which is similar to increasing the number of turns in the solenoid. From Ampere's Law and the functioning of a solenoid, it is known that the magnetic field strengths that can be generated are inversely proportional to the length of the solenoid and directly proportional to the number of turns in the solenoid. More precisely, the solenoid formula can be written as $$B = \mu_0 \mu_r n I \qquad \text{(Equation 1)}$$

In Equation 1, $\mu_0$ is the magnetic permeability of free space and $\mu_r$ is the relative permeability of a ferrite core. In Equation 1, n is the number of turns per unit length of the solenoid and I is the current through the solenoid. Thus relatively large magnetic fields can be achieved which, when modulated via the modulation of the AC current, yields large electric field gradients as observed in the simulations. It can also be concluded from Equation 1 that the magnetic field created on-axis for a 2D current loop is as follows:

$$B = \frac{\mu_0}{4\pi} \frac{2\pi R^2 NI}{4\pi (z^2 + R^2)^{\frac{3}{2}}} H \qquad \text{(Equation 2)}$$

In Equation 2, z is the distance along the axis away from the coil, R is the radius of the coil, I is the current and N is the number of loops. At a given distance and for a given radius, the magnetic field can be increased by increasing the number of loops.

In FIG. 10A, the electric field gradients in the same multi-loop multi-core design are plotted along a longitudinal cross-section shown by the line 901. In the several regions where the high permeability cores come in close proximity to the traces, there is a sharp increase in the electric field strength in the spatial electric field gradient, reaching values of greater than $10^7$ V/m$^2$. The number of such spatial locations where strong electric field gradients are obtained can be adjusted by changing the number of loops and ferrite cores involved. Although the electric field gradient is higher than the neural activation threshold value of 11000 V/m$^2$ above the innermost core, this can be reduced by reducing the currents from the value of 50 mA used in these examples.

Figure 11:
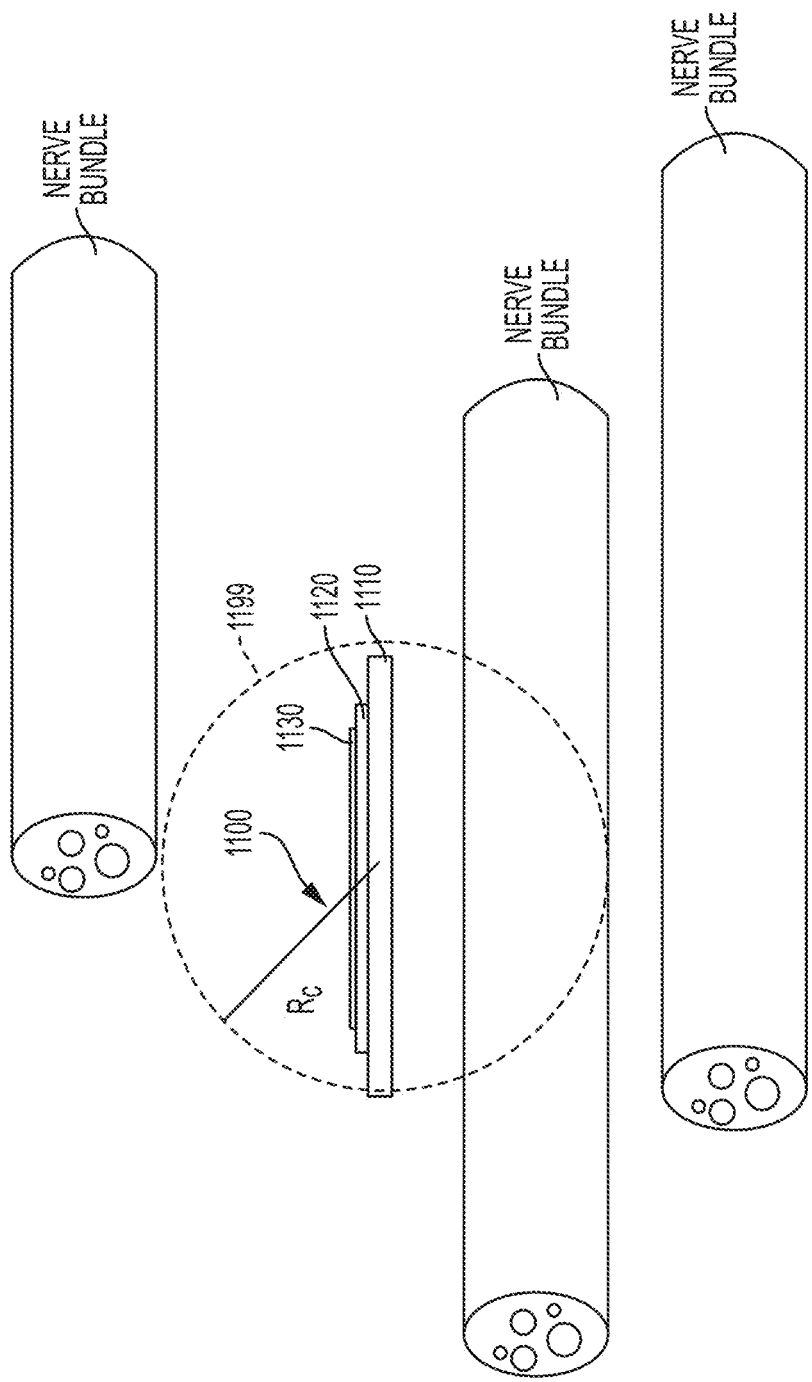
FIG. 11 illustrates the excitation volume of a magnetic probe in accordance with some embodiments.
Figure 12:
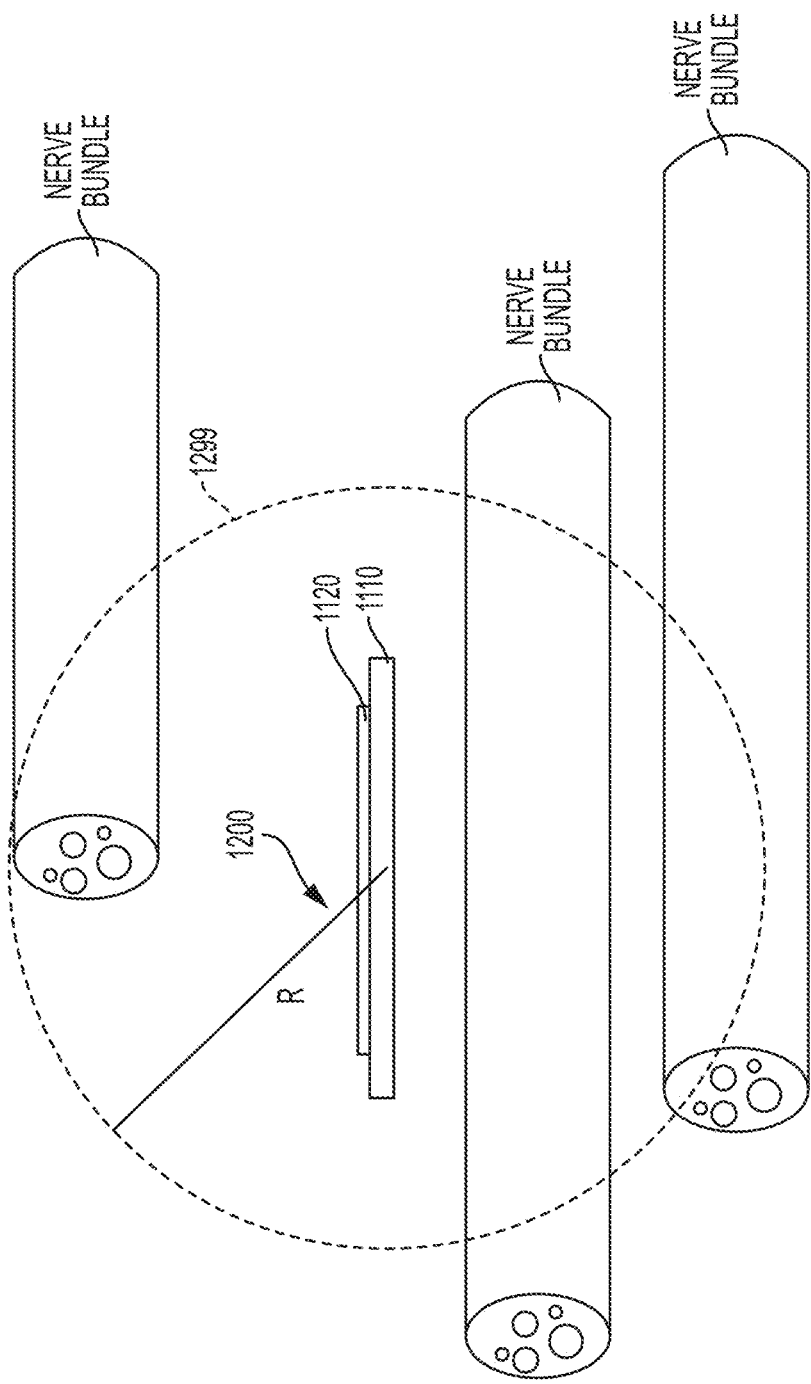
FIG. 12 illustrates the excitation volume of a comparative magnetic probe that does not include magnetic cores.

FIG. 11 illustrates the operation of the disclosed magnetic probe 1100 in accordance with some embodiments. Probe 1100 includes at least one electrical conductor 1120 disposed on a substrate 1110 and forming at least one loop with at least one magnetic core 1130 disposed within the loop. When energized by a current through the loop, probe 1100 has an activation volume 1199 with radius Rc. The electric field gradient within the activation volume 1199 is generally sufficient to activate neurons and the electric field gradient outside the activation volume 1199 is generally insufficient to activate neurons. When compared to a substantially similar probe that does not include the at least one magnetic core, for the same energizing current and the same electric field gradient, the activation volume in the probe with the magnetic core may be reduced by at least a few percent to about 60%, for example.

In general, the electric current through the loop formed by the electrical conductor 1120 may be less than about 500 mA, or less than 250 mA, or less than 100 mA, or less than 50 mA or even less than about 25 ma to obtain the electric field gradients discussed herein. When energized by an electric current in a range of about 25 mA to about 500 mA, e.g., a current of about 25 mA, 50 mA, about 100 mA, about 200 mA, or about 500 mA through the loop, the probe is configured to produce a spatial electric field gradient between about $10^4$ V/m$^2$ to about $10^7$ V/m$^2$ within a volume around the probe. The volume may have a radius less than 150 µm to less than about 25 µm, for example. For example, the probe may produce an electric field gradient greater than $10^4$ V/m$^2$ inside the volume and a spatial electric field gradient less than $10^4$ V/m$^2$ at and beyond the boundary of the volume. In another example, the probe may produce a spatial electric field gradient greater than $10^5$ V/m$^2$ inside the volume and a spatial electric field gradient less than $10^5$ V/m$^2$ at and beyond the boundary of the volume. In another example, the probe may produce a spatial electric field gradient greater than $10^6$ V/m$^2$ inside the volume and a spatial electric field gradient less than $10^6$ V/m$^2$ outside the volume. In yet another example, the probe may produce a spatial electric field gradient greater than $10^7$ V/m$^2$ inside the volume and a spatial electric field gradient less than $10^7$ V/m$^2$ at and beyond the boundary of the volume. When compared to a substantially similar probe that does not include the at least one magnetic core, for the same energizing current and the same electric field gradient, the volume may be reduced by at least a few percent to about 60%.

Figure 13:
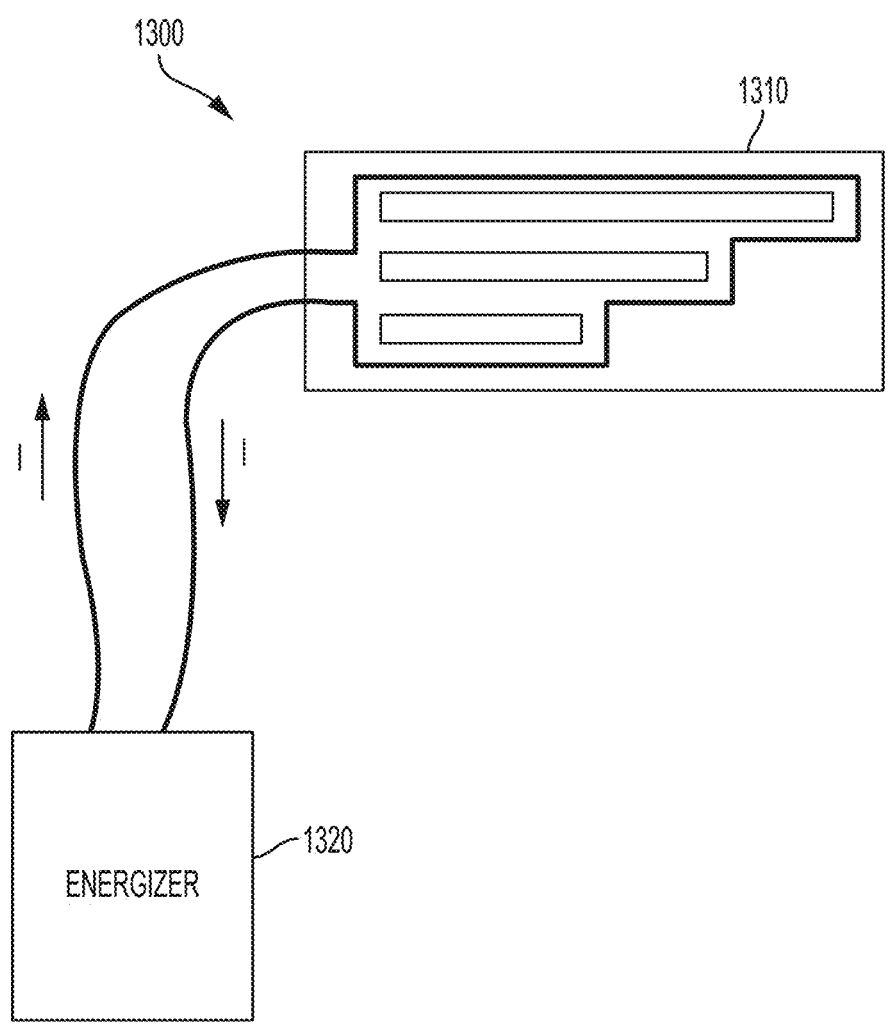
FIG. 13 is a block diagram of a neurostimulation system in accordance with some embodiments.

As previously discussed, the magnetic probe disclosed herein finds application as a neural stimulation probe. FIG. 13 illustrates a neural stimulation system 1300 that incorporates the disclosed magnetic probe 1310. The probe 1310 may be configured for implantation within the body of an organism, e.g., a mammal such as a human. In various implementations, the probe 1310 may be used in vivo or in vitro. The electrical conductor forming the loop of the probe 1310 is electrically connected to an energizer 1320 by leads 1315. The energizer 1320 produces an electrical current, I, e.g., an alternating electrical current (AC current) that flows through the leads 1315 and through the loop of the probe. The current, I, generates a magnetic field and an electric field gradient. When the magnetic probe 1310 is energized by the current, I, the electric field gradient produced by the magnetic probe 1310 is sufficient to activate neurons within an activation volume around the probe 1310. In some embodiments, the leads 1315 and/or the energizer 1320 may be configured for implantation.

By using high permeability cores, the volume of activation can be confined above the threshold value for neural stimulation of 11000 V/m$^2$. For example, for the same current values of 15 mA, simulations demonstrate a reduction of the radius of activation by up to 3 fold. This will thus permit driving larger currents into the loops and thus obtain larger electric field gradients, while not compromising on the selectivity of the excitation volume.

Extending the concept of a 3D solenoid or the 2D current loop to the 2D plane, multi-loop and multi-core magnetic probes have been designed that increase the electric field gradients produced by the probe. These designs can restrict activation depth of the probe by about 3 times when compared to probes without the cores for the same currents driven.

The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

The invention claimed is:

1. An implantable magnetic neurostimulation probe, comprising:
   at least one substrate;
   at least one electrical conductor disposed on the at least one substrate and arranged in at least one planar loop, the at least one electrical conductor configured to produce an electric field sufficient to activate neurons;
   at least one planar magnetic core comprising a magnetic material disposed on the at least one substrate and within the at least one planar loop; and
   a biocompatible coating disposed over the at least one substrate, the at least one electrical conductor, and the at least one planar magnetic core, wherein:
   the at least one electrical conductor is arranged such that the at least one planar loop comprises multiple sections within the at least one planar loop; and
   the at least one planar magnetic core comprises multiple magnetic cores, each magnetic core disposed within a respective one of the multiple sections.

2. The probe of claim 1, wherein the multiple magnetic cores include at least a first magnetic core having a first surface area and a second magnetic core having a second surface area that is different from the first surface area.

3. The probe of claim 1, wherein at least one side of the at least one planar loop has a sawtooth profile.

4. The probe of claim 3, wherein the at least one planar loop having the sawtooth profile comprises:
   multiple sections, each of the multiple sections having an area that differs from an area of other sections of the multiple sections; and
   each of the multiple magnetic cores having a surface area that differs from a surface area of other magnetic cores of the multiple magnetic cores.

5. The probe of claim 1, wherein the at least one planar loop is a single electrically continuous loop.

6. The probe of claim 1, wherein the at least one electrical conductor comprises an electrically continuous electrical conductor that forms multiple concentric loops arranged in a spiral.

7. The probe of claim 1, wherein the at least one planar loop comprises multiple planar loops.

8. The probe of claim 7, wherein the multiple planar loops are concentric.

9. The probe of claim 8, wherein each of the multiple magnetic core is disposed within a respective one of the multiple concentric planar loops.

10. The probe of claim 1, wherein:
    the at least one substrate is one or both of flat and rigid; and
    the at least one electrical conductor and the at least one planar magnetic core conform to the at least one substrate.

11. The probe of claim 1, wherein the magnetic material has a magnetization change per cm$^3$ mol$^{-1}$ in a range of about 10 to 2000 G.

12. The probe of claim 1, wherein, when energized by an electric current of about 50 mA through the at least one loop, the probe is configured to produce an excitation volume having a boundary with a radius of about 50 µm such that at an electric field gradient generated by the probe is greater than 11000 V/m$^2$ within the boundary and is less than 11000 V/m$^2$ at and beyond the boundary.

13. The probe of claim 12, wherein the electric field gradient generated by the probe is greater than $10^6$ V/m$^2$ within the boundary and is less than $10^6$ V/m$^2$ at and beyond the boundary.

14. The probe of claim 1, wherein, when energized by an electric current having a predetermined value through the at least one planar loop, the probe has an activation volume with a radius that is up to about 60% less than a radius of an activation volume of an otherwise identical probe without the at least one planar magnetic core that is energized by the predetermined value of the electric current.

15. A system, comprising:
an implantable magnetic neurostimulation probe comprising:
  at least one substrate;
  at least one electrical conductor disposed on the at least one substrate and arranged as at least one planar loop, the at least one electrical conductor configured to produce an electric field sufficient to activate neurons;
  at least one planar magnetic core comprising a magnetic material disposed on the at least one substrate and within the at least one planar loop; and
  a biocompatible coating disposed over the at least one substrate, the at least one electrical conductor, and the at least one planar magnetic core; and
an energizer configured to apply an electrical current through the at least one electrical conductor, wherein:
  the at least one electrical conductor is arranged such that the at least one planar loop comprises multiple sections within the at least one planar loop; and
  the at least one planar magnetic core comprises multiple magnetic cores, each magnetic core disposed within a respective one of the multiple sections.

16. An implantable magnetic neurostimulation probe, comprising:
  at least one substrate;
  at least one electrical conductor disposed on the at least one substrate and arranged in at least one planar loop, the at least one electrical conductor configured to produce an electric field sufficient to activate neurons;
  at least one planar magnetic core comprising a magnetic material disposed on the at least one substrate and within the at least one planar loop; and
  a biocompatible coating disposed over the at least one substrate, the at least one electrical conductor, and the at least one planar magnetic core, wherein:
  the at least one planar loop comprises multiple planar loops;
  the multiple planar loops are concentric; and
  the at least one planar magnetic core comprises multiple magnetic cores, each of the multiple magnetic cores disposed within a respective one of the multiple concentric planar loops.

17. The probe of claim 16, wherein the at least one electrical conductor comprises an electrically continuous electrical conductor that forms the multiple planar loops.

18. The probe of claim 17, wherein the multiple concentric loops are arranged in a spiral.

19. The probe of claim 16, wherein, when energized by an electric current having a predetermined value through the at least one planar loop, the probe has an activation volume with a radius that is up to about 60% less than a radius of an activation volume of an otherwise identical probe without the at least one planar magnetic core that is energized by the predetermined value of the electric current.

20. An implantable magnetic neurostimulation probe, comprising:
  at least one substrate;
  at least one electrical conductor disposed on the at least one substrate and arranged in at least one planar loop, the at least one electrical conductor configured to produce an electric field sufficient to activate neurons;
  at least one planar magnetic core comprising a magnetic material disposed on the at least one substrate and within the at least one planar loop; and
  a biocompatible coating disposed over the at least one substrate, the at least one electrical conductor, and the at least one planar magnetic core;
  wherein, when energized by an electric current of about 50 mA through the at least one loop, the probe is configured to produce an excitation volume having a boundary with a radius of about 50 μm such that at an electric field gradient generated by the probe is greater than 11000 V/m$^2$ within the boundary and is less than 11000 V/m$^2$ at and beyond the boundary.

21. The probe of claim 20, wherein the electric field gradient generated by the probe is greater than $10^6$ V/m$^2$ within the boundary and is less than $10^6$ V/m$^2$ at and beyond the boundary.

22. An implantable magnetic neurostimulation probe, comprising:
  at least one substrate;
  at least one electrical conductor disposed on the at least one substrate and arranged in at least one planar loop, the at least one electrical conductor configured to produce an electric field sufficient to activate neurons;
  at least one planar magnetic core comprising a magnetic material disposed on the at least one substrate and within the at least one planar loop; and
  a biocompatible coating disposed over the at least one substrate, the at least one electrical conductor, and the at least one planar magnetic core;
  wherein, when energized by an electric current having a predetermined value through the at least one planar loop, the probe has an activation volume with a radius that is up to about 60% less than a radius of an activation volume of an otherwise identical probe without the at least one planar magnetic core that is energized by the predetermined value of the electric current.

23. The probe of claim 22, wherein:
the probe is configured to produce an excitation volume having a boundary; and
an electric field gradient generated by the probe is greater than $10^6$ V/m$^2$ within the boundary and is less than $10^6$ V/m$^2$ at and beyond the boundary.

\* \* \* \* \*